United States Patent [19]

Wittmer

[11] 4,415,264

[45] Nov. 15, 1983

[54] SPECTROPHOTOMETER GAS CONTROL SYSTEM

[75] Inventor: Charles M. Wittmer, Trumbull, Conn.

[73] Assignee: The Perkin-Elmer Corporation, Norwalk, Conn.

[21] Appl. No.: 277,351

[22] Filed: Jun. 25, 1981

[51] Int. Cl.³ .................... F23N 5/08; G01N 21/72
[52] U.S. Cl. .................................. 356/315; 250/554; 431/79
[58] Field of Search .............. 356/315, 417; 250/554; 431/79

[56] References Cited

U.S. PATENT DOCUMENTS 3,583,844  6/1971  Smith, Jr. ........................ 356/315
3,586,441  6/1971  Smith et al. ..................... 356/315

Primary Examiner—F. L. Evans
Attorney, Agent, or Firm—S. A. Giarratana; F. L. Masselle; R. A. Hays

[57] ABSTRACT

This invention relates to a spectrophotometer which includes a burner adapted for burning a gaseous fuel and for atomizing a sample to be analyzed in a burner compartment, mechanical elements or electrical circuitry serving to periodically pass a beam of light through the burner compartment, a detector, electrical circuitry for energizing the detector during the period of absence of the beam of light through the burner compartment, said detector being adapted when energized to produce an electronic signal representative of the presence of a flame in the burner compartment; and control elements responsive to the electronic signal for controlling the feeding of fuel to the burner.

6 Claims, 1 Drawing Figure

U.S. Patent
Nov. 15, 1983
4,415,264
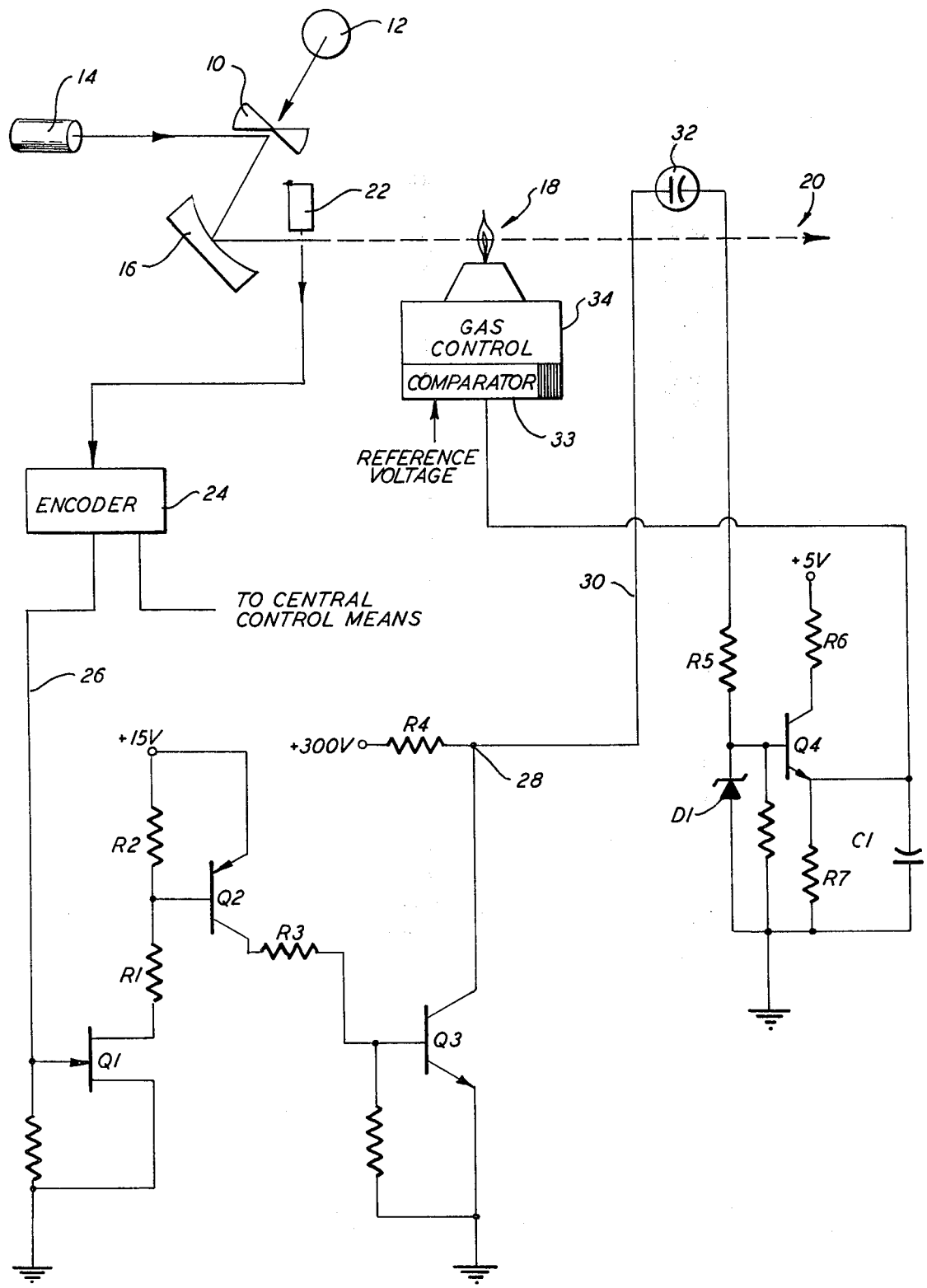

SPECTROPHOTOMETER GAS CONTROL SYSTEM

BACKGROUND OF THE INVENTION

The present invention relates to a gas control system for a spectrophotometer, which is particularly adapted, among other possible uses, for use in atomic absorption spectroscopy.

In atomic absorption spectroscopy, the measurement of the absorption of a radiation beam at a characteristic resonant spectral line for a particular element yields a measure of the concentration of that element in an original sample solution. Presently, one of the most common techniques for atomizing an element for purposes of the absorption measurement, is by introducing a liquid sample solution of the element of interest into a gas burner wherein droplets of the solution are vaporized and the elements ultimately atomized, so as to form in the path of the apparatus radiation beam, a substantial quantity of the element of interest in its atomic state. A sample light beam, which originates from a line-emitting light source, and which includes a resonance line of the element to be measured, is directed through the furnace. The desired element in the sample absorbs the resonance lines characteristic of the element and the emerging light beam is directed to a monochromator and thence to a detector which measures the degree to which the desired element absorbs the resonance lines of the sample beam. This absorption degree represents the amount of desired element in the sample substance.

In some installations, a double beam from the light-emitting source is employed, and in other installations a second double beam from a light source having a continuous spectrum is used, with optical beam-switching choppers to sequentially direct the various beams through the system. In other installations, electrically pulsed operation of the signal and background source is effected in lieu of a mechanical chopper.

Difficulties were experienced with prior art such instruments, when the flame went out, but the fuel and oxidant were still being supplied to the burner. Attempts were made to reduce the hazard by positioning an ultraviolet detector within the burner chamber. The detector was then relied on to indicate the absence of a flame and send out a signal so that the supply of fuel oxidant could be terminated. However, such detectors frequently produced signals, which erroneously represented the presence of a flame when in fact, none existed. Such signals were created by the presence of reflected light, for example, from the measuring beam or from some other outside source, within the chamber. One technique developed to reduce such erroneous signals resided in reducing the light entry aperture of the UV detector. This, however, was not entirely effective. Another technique was to point the aperture of the detector in a direction, which reduced the number of reflections reaching the aperture. This, also, was not entirely effective.

It will be appreciated that the above-mentioned hazardous condition was further aggravated when the instrument operator attempted to improve the sensitivity of the instrument by utilizing a relatively lean gas mixture. In such instruments it was often necessary to install an override feature, which electrically isolated the detector to prevent it from giving off any signals, during the time when lean gas mixtures were being used. This, of course, completely eliminated this safety feature during such operation.

It is, therefore, an object of the present invention to provide an apparatus, which more accurately determines the absence of a flame from a gas burner in a spectrophotometer.

SUMMARY OF THE INVENTION

Briefly, my invention comtemplates the provision of a new and improved spectrophotometer, which includes a burner adapted for burning a gaseous fuel in a burner compartment, means for periodically passing a beam of light through the burner compartment, a detector, means for energizing said detector during the period of absence of said beam of light through the burner compartment, said detector being adapted when energized to produce an electronic signal representative of the presence of a flame in said burner compartment, and means responsive to the electronic signal for controlling the flow of fuel fed to the burner.

According to one aspect of the invention, the means responsive to the electronic signal for controlling the flow of fuel fed to the burner includes switching means having a constant time delay network responsive to the output of the detector. This switching means, having a constant time delay network, includes in one form thereof a transistor having its collector connected through a resistor to a voltage source and having its emitter connected to a capacitor and resistor connected in parallel to ground, said emitter also being connected to control means for said burner, and the base of the transistor being connected to the output of said detector.

In one form of the invention, the means for periodically passing the beam of light through the burner compartment includes a chopper assembly, and the means for energizing the detector during the period of absence of said beam of light through the burner compartment comprises a chopper position sensor, with switching means responsive to said chopper position sensor for directing a source of voltage to the detector for energizing same. In one form of the invention, the electronic switching means employs semiconductor elements.

There has thus been outlined rather broadly the more important features of the invention in order that the detailed description thereof that follows may be better understood, and in order that the present contribution to the art may be better appreciated. There are, of course, additional features of the invention which will be described more fully hereinafter. Those skilled in the art will appreciate that the conception on which this disclosure is based may readily be utilized as a basis for the design of other arrangements for carrying out the several purposes of the invention. It is important, therefore, that this disclosure be regarded as including such equivalent arrangements as do not depart from the spirit or scope of the invention.

One embodiment of the invention has been chosen for the purposes of illustration and description, and is shown in the accompanying drawing, forming a part of this specification.

BRIEF DESCRIPTION OF THE DRAWING

The single FIGURE of the drawing is a diagrammatic representation of a portion of an instrument embodying the principles of the present invention.

DETAILED DESCRIPTION OF THE INVENTION

The drawing shows an example of the circuit of the invention integrated with a schematic diagram of a background corrected spectrophotometer, using a gas control system with a flow sensor control. Only the sample beam is shown, because the invention will work with either a single beam or a double beam optical system. Further, the system of the invention will also work with an electronically pulsed operation of the signal and background light source in lieu of the mechanical rotating chopper shown in the drawing.

Referring to the drawing, the spectrophotometer includes an optical beam-switching chopper 10, which may, for example, be of the type described in U.S. Pat. No. 4,168,910. This chopper is arranged to alternately pass and block the passage of light from a first source such as a deuterium arc lamp 12, as well as from a second light source, such as a hollow cathode or electrodeless discharge lamp 14. In certain positions of the chopper, radiation is blocked from both sources. This is referred to as "dark time" by those skilled in the art. The beam which passes through the chopper 10 is directed through an optical system, indicated schematically at 16 to a burner 18, which ignites the fuel, oxidant and sample mixture. The measurement of the absorption of the radiation beam at a characteristic resonant spectral line for a particular element yields a measure of the concentration of that element in an original sample. Thus, the beam of radiation after passing through the flame of burner 18 is directed to a monochromator, detector and electronics, as indicated generally at 20 in the drawing.

Adjacent the chopper 10 is an optical position sensor 22, which may, for example, include means such as a light emitting diode for providing a light output to a photosensor device, which is used to sense the chopper 10 and provide an appropriate electrical output to an encoder 24, which may, for example, be a Perkin-Elmer part No. 0047-9784, as sold by The Perkin-Elmer Corporation of Norwalk, Connecticut. As is conventional, this encoder sends a signal representative of the position of the chopper 10, to the central control means (not shown) of the spectrophotometer for purposes of coordinating the functions of the various components of the system. In addition, the encoder 24 outputs a signal on conductor 26, said signal being low when the light from both sources is blocked, i.e., dark time, and high at all other times. The state of conductor 26 controls a grounding switch $Q_1$. One side of $Q_1$ is connected to a +15 volt source through resistors $R_1$ and $R_2$, while the other side is connected to ground. The base of a PNP type transistor $Q_2$ is connected between resistors $R_1$ and $R_2$, and the emitter is connected to the +15 volt source. The collector of transistor $Q_2$ is connected through resistor $R_3$ to the base of NPN transistor $Q_3$, the emitter of which is connected to ground and the collector is connected to a +300 volt source through a junction 28 and resistor $R_4$. Thus, transistor $Q_1$ and $Q_2$ are phasing and level shifters so as to control transistor $Q_3$ utilizing the conventional spectrophotometer encoder 24.

Still referring to the drawing, a conductor 30 connects the junction 28 to the input of a flame radiation detector 32 which may, for example, be a UVtron type R259 radiation detector, as manufactured by the Hamamatsu Corporation of Middlesex, N.J. The detector 32 is positioned adjacent the flame of the burner 18, as will be described more fully hereinafter. The output from the detector 32 is connected to the base of an NPN transistor $Q_4$ through a resistor $R_5$. Included in the base circuit of the transistor $Q_4$ is a zener diode $D_1$ which serves to clamp the voltage at a preselected value when the base goes high. The collector of transistor $Q_4$ is connected through resistors $R_6$ to a +5 volt source, and the emitter thereof is connected to a network which includes a resistor $R_7$ and a capacitor $C_1$ connected in parallel to ground. The emitter is also connected to the input of a comparator 33. The comparator receives a reference voltage, and if the voltage received from the transistor $Q_4$ is below the reference voltage, the comparator will output a signal to the burner controller 34, indicating that the flame is off, and to automatically shut off the fuel and oxidant sources. Any suitable burner controller may be employed, such as, for example, model 0047-0560, as manufactured by The Perkin-Elmer Corporation of Norwalk, Conn.

In operation, a dark time signal occurs when both the signal and the background light sources are optically off. At that time the flame sensor is turned on to detect the actual flame, and therefore, no spurious light is fed into the flame sensor via the reflections in the burner compartment. In the embodiment illustrated, during the dark time portion of the cycle, the output of the encoder 24 along conductor 26 is low, thereby making the grounding switch $Q_1$ conductive which, in turn, makes the base of transistor $Q_2$ low, and hence non-conductive. This makes the base of the transistor $Q_3$ low and hence this transistor is non-conductive. Since transistor $Q_3$ is non-conductive, the +300 volt source is directed to the flame sensor 32. That is, when transistor $Q_3$ is off, it turns the flame sensor on in its normal mode of operation.

If ultraviolet light is detected from the burner flame and the plate voltage is applied to the flame sensor, it will allow current to flow into the cathode of the zener diode $D_1$ at the base of the transistor $Q_4$. The emitter of the transistor $Q_4$ will then charge the capacitor $C_1$. When the flame sensor is turned off, or if the flame is off, the charge will remain stored in the resistor $R_7$ and capacitor $C_1$ network with its appropriate time constant. If the voltage level is more than a preselected level, such as, for example, 1.5 volts, the high impedance level comparator in the gas burner control will indicate that the burner flame is on and allow the fuel and the oxidant flow to continue. When the flame is extinguished, the current will cease being charged into the capacitor $C_1$ and the voltage will decay to less than the preselected level and the gas burner comparator and controller will indicate that the flame is off. The system will then automatically shut-off the fuel and oxidant sources.

I have found that by synchronizing the electronic control of the sensor with the dark time processing of the spectrophotometer, I provide a rejection ratio of better than 50 to 1 for a worst condition of a strong light source, such as a deuterium arc lamp, shining directly into the UV radiation flame detector. This compares with other techniques, such as using an optical slit in front of the flame detector, which produces rejection ratios of between 10 and 2 to 1 for ordinary stray light burner applications. This ratio improvement between the actual flame condition and spurious stray light provides additional safety enhancement for the gas burner system, and in addition it allows the system sensitivity to be increased. This is particularly important for lean flame conditions and therefore provides additional operator convenience without the necessity of using an additional override control.

Although a certain embodiment of the invention is herein disclosed for the purposes of explanation, further modification thereof, after study of this specification, will be apparent to those skilled in the art to which the invention pertains. Reference should accordingly be had to the appended claims in determining the scope of the invention.

What is claimed and desired to be secured by Letters Patent is:

1. A spectrophotometer comprising, in combination:
   a burner for burning a gaseous fuel and for atomizing a sample to be analyzed in a burner compartment;
   means for periodically passing a beam of light through the burner compartment;
   a detector;
   means for energizing said detector during the period of absence of said beam of light through said burner compartment;
   said detector being adapted when energized to produce an electronic signal representative of the presence or absence of a flame in said burner; and
   means responsive to said electronic signal, for controlling the feeding of the fuel to said burner.

2. A spectrophotometer according to claim 1, wherein said means responsive to said electronic signal for controlling the feeding of fuel to said burner include switching means having a constant time delay network responsive to the output of said detector.

3. A spectrophotometer according to claim 2, wherein said switching means having a constant time delay network comprises a transistor having its base connected to the output of said detector and having its collector connected through a resistor to a voltage source and having its emitter connected to a capacitor and a resistor connected in parallel to ground, said emitter being also connected to control means for said burner.

4. A spectrophotometer according to claim 1 wherein said means for periodically passing a beam of light through the burner compartment comprises a rotary mechanical chopper assembly.

5. A spectrophotometer according to claim 4 wherein said means for energizing said detector comprises a chopper position sensor, and switching means responsive to said chopper position sensor for directing a source of voltage to said detector for energizing said detector during the period of absence of said beam of light through the burner compartment.

6. A spectrophotometer according to claim 5 wherein said switching means comprises an electronic switch employing semiconductor elements.

* * * * *